United States Patent
Yoshizawa et al.

(10) Patent No.: US 11,886,834 B2
(45) Date of Patent: Jan. 30, 2024

(54) ELECTRONIC DEVICE, INPUT-DATA PROCESSING METHOD, AND STORAGE MEDIUM

(71) Applicant: CASIO COMPUTER CO., LTD., Tokyo (JP)

(72) Inventors: Hiroaki Yoshizawa, Ome (JP); Hironori Yoshikawa, Sagamihara (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 256 days.

(21) Appl. No.: 17/532,762

(22) Filed: Nov. 22, 2021

(65) Prior Publication Data
US 2022/0206752 A1  Jun. 30, 2022

(30) Foreign Application Priority Data
Dec. 25, 2020  (JP) ................................. 2020-216801

(51) Int. Cl.
  *G06F 7/544* (2006.01)
  *G06F 3/0489* (2022.01)
(52) U.S. Cl.
  CPC ............ *G06F 7/544* (2013.01); *G06F 3/0489* (2013.01)
(58) Field of Classification Search
  CPC ......... G06F 7/544; G06F 7/575; G06F 3/0489
  See application file for complete search history.

(56) References Cited

U.S. PATENT DOCUMENTS

| 6,295,544 B1 * | 9/2001 | Cheung ................. G06F 15/025 708/134 |
| 2017/0178838 A1 * | 6/2017 | Ohira ................... H03K 17/962 |
| 2018/0081851 A1 * | 3/2018 | Arikawa ................. G06F 15/02 |

FOREIGN PATENT DOCUMENTS

| JP | S63098018 A | 4/1988 |
| JP | 2000056883 A | 2/2000 |

OTHER PUBLICATIONS

Ee Sian Neo et al., A Switching Command-Based Whole-Body Operation Method for Humanoid Robots, Oct. 1, 2005, IEEE/ASME Transactions on Mechatronics, vol. 10, No. 5, pp. 546-559 (Year: 2005).*
Rupak Majumdar et al., Systematic Testing for Control Applications, Jul. 1, 2010, IEEE Xplore, pp. 1-10 (Year: 2010).*
Japanese Office Action dated Jan. 7, 2023 (and English translation thereof) issued in counterpart Japanese Application No. 2020-216801.

* cited by examiner

*Primary Examiner* — Tam T Tran
(74) *Attorney, Agent, or Firm* — Holtz, Holtz & Volek PC

(57) ABSTRACT

An electronic device including a processor configured to execute a program stored in a memory, in which the processor executes input-screen display processing of causing a display to display an input screen, in order to accept input of data for a certain item, executes, when the input of the data for the certain item is accepted by a first method during display of the input screen, default-value setting processing of setting the data as a default value for the certain item, and executes data processing with the data, and executes, when the input of the data for the certain item is accepted by a second method during display of the input screen, default-value non-setting processing of not setting the data as the default value, and executes the data processing with the data.

19 Claims, 9 Drawing Sheets

*FIG. 6A*

| VARIABLE NAME | INPUT-VALUE HOLDING FLAG | CALCULATION-EXECUTION DEDICATED MEMORY | HELD-NUMERIC-VALUE MEMORY |
|---|---|---|---|
| SINGLE-PACKET WEIGHT | ON | 0.6 | 0 |
| SINGLE-MEDICINE WEIGHT | OFF | 2 | 0 |
| NUMBER OF POWDERED MEDICINES | OFF | 9 | 0 |
| DISPENSING ERROR | ON | 2 | 0 |

*FIG. 6B*

| VARIABLE NAME | INPUT-VALUE HOLDING FLAG | CALCULATION-EXECUTION DEDICATED MEMORY | HELD-NUMERIC-VALUE MEMORY |
|---|---|---|---|
| SINGLE-PACKET WEIGHT | ON | 0.6 | 0.6 |
| SINGLE-MEDICINE WEIGHT | OFF | 2 | 0 |
| NUMBER OF POWDERED MEDICINES | OFF | 9 | 0 |
| DISPENSING ERROR | ON | 2 | 2 |

FIG. 7A

| VARIABLE NAME | INPUT-VALUE HOLDING FLAG | CALCULATION-EXECUTION DEDICATED MEMORY | HELD-NUMERIC-VALUE MEMORY |
|---|---|---|---|
| SINGLE-PACKET WEIGHT | ON | 0 | 0.6 |
| SINGLE-MEDICINE WEIGHT | OFF | 0 | 0 |
| NUMBER OF POWDERED MEDICINES | OFF | 0 | 0 |
| DISPENSING ERROR | ON | 0 | 2 |

FIG. 7B

| VARIABLE NAME | INPUT-VALUE HOLDING FLAG | CALCULATION-EXECUTION DEDICATED MEMORY | HELD-NUMERIC-VALUE MEMORY |
|---|---|---|---|
| SINGLE-PACKET WEIGHT | OFF | 0.8 | 0.6 |
| SINGLE-MEDICINE WEIGHT | OFF | 3 | 0 |
| NUMBER OF POWDERED MEDICINES | OFF | 4 | 0 |
| DISPENSING ERROR | OFF | 5 | 2 |

FIG. 7C

| VARIABLE NAME | INPUT-VALUE HOLDING FLAG | CALCULATION-EXECUTION DEDICATED MEMORY | HELD-NUMERIC-VALUE MEMORY |
|---|---|---|---|
| SINGLE-PACKET WEIGHT | ON | 0.8 | 0.8 |
| SINGLE-MEDICINE WEIGHT | OFF | 3 | 0 |
| NUMBER OF POWDERED MEDICINES | OFF | 4 | 0 |
| DISPENSING ERROR | OFF | 5 | 2 |

*FIG. 8*

ELECTRONIC DEVICE, INPUT-DATA PROCESSING METHOD, AND STORAGE MEDIUM

BACKGROUND

1. Technical Field

The present disclosure relates to an electronic device to which data is input for a plurality of items, an input-data processing method that the electronic device executes, and a storage medium.

2. Related Art

Conventionally, in a device that processes data, executed is processing of repeating input for each item in a data set including one or more items as data input targets, for a plurality of data sets. For example, in the information processing system described in JP S63-98018 A, a plurality of items are provided as parameters, and data is repeatedly input for the plurality of items.

In the information processing system described in JP 63-98018 A, a default value and an input permission condition are input as parameters, and a value satisfying the input permission condition is passed to an input target item on a screen for the subsequent data input and displayed thereon.

SUMMARY

An electronic device including at least one processor configured to execute a program stored in at least one memory,
in which the at least one processor
executes input-screen display processing of causing a display to display an input screen, in order to accept input of data for a certain item,
executes, in a case where the input of the data for the certain item is accepted by a first method during display of the input screen, default-value setting processing of setting the data as a default value for the certain item, and executes data processing with the data of which the input is accepted by the first method, and
executes, in a case where the input of the data for the certain item is accepted by a second method different from the first method during display of the input screen, default-value non-setting processing of not setting, as the default value for the certain item, the data of which the input is accepted, and executes the data processing with the data of which the input is accepted by the second method.

BRIEF DESCRIPTION OF THE DRAWINGS

FIGS. 6A and 6B each illustrate a specific example of a memory image for describing a calculation function of the calculator according to the first embodiment;

FIGS. 7A to 7C each illustrate a specific example of a memory image for describing a calculation function of the calculator according to the first embodiment;

FIG. 8 illustrates a specific example of a data input operation and display for describing a calculation function of a calculator according to a second embodiment.

DETAILED DESCRIPTION

Hereinafter, embodiments of the present disclosure will be described with reference to the accompanying drawings.

Figure 1:
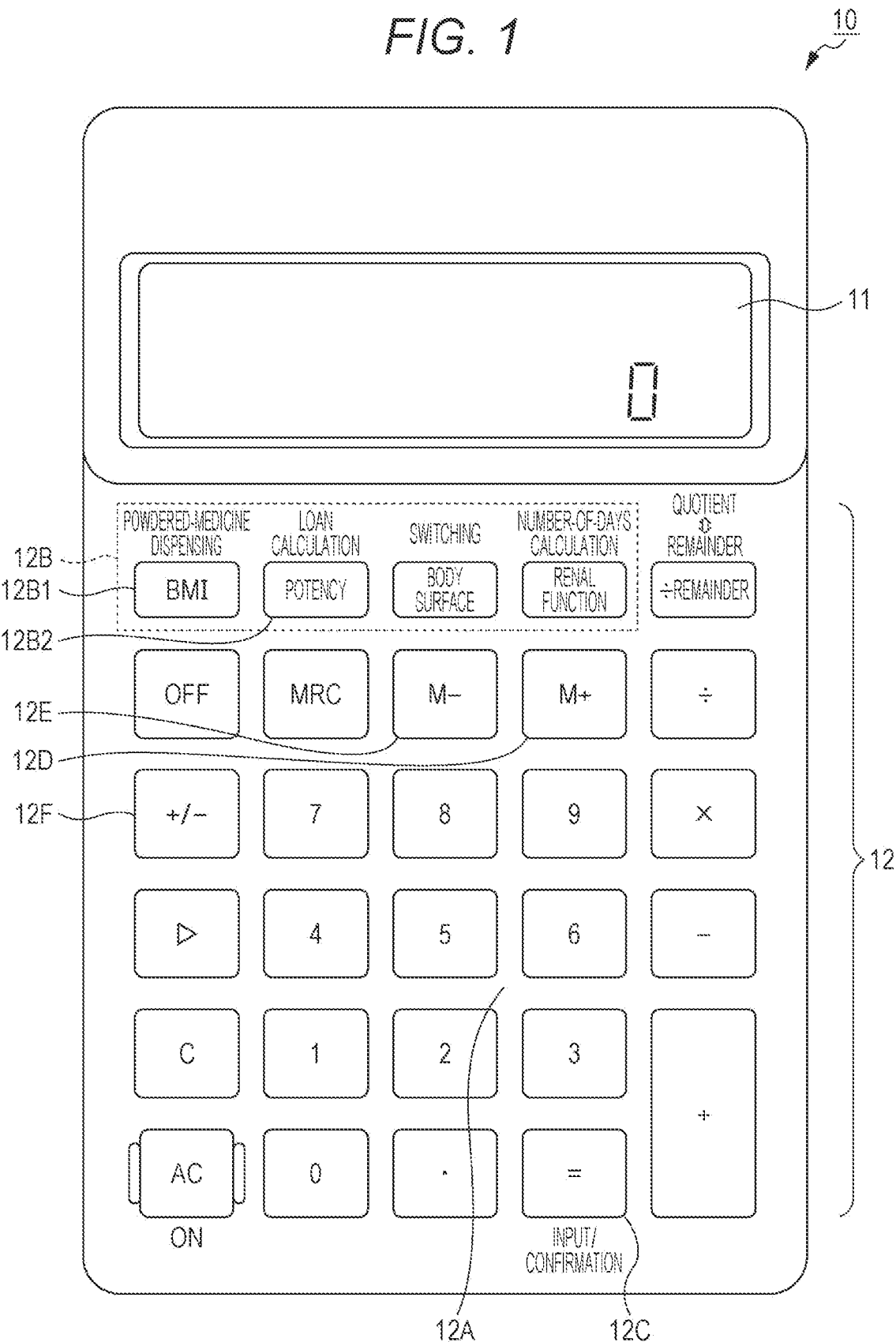
FIG. 1 illustrates a configuration of an electronic device according to the present embodiment.

FIG. 1 illustrates a configuration of an electronic device according to the present embodiment. As illustrated in FIG. 1, the electronic device according to the present embodiment provided as, for example, a calculator 10.

Note that the electronic device can be provided not only as the calculator 10 but also, for example, any of a personal computer, a tablet computer, a smartphone, a mobile phone, a personal digital assistant (PDA), an electronic book, a portable game device, and a car navigation system that have a calculation function (with a calculation program embedded therein). Note that, unlike the calculator 10, a calculator without physical keys (buttons) mounted thereon displays a software keyboard similar to the keys of the calculator 10, and executes calculation processing by data input in response to a key operation on the software keyboard.

As illustrated in FIG. 1, the calculator 10 according to the present embodiment includes a display unit 11 and a key input unit 12 on the front face of the main body.

The display unit 11 includes, for example, a monochrome reflective liquid crystal display panel. For example, the display unit 11 is provided with, for example, a dot-matrix display section in the upper part and a seven-segment display section in the lower part. The dot-matrix display section can display, for example, characters indicating an operation guide, setting information, and an input data unit. In the seven-segment display section, for example, seven segments for displaying numeric characters for 10 digits and a decimal segment are arranged, and the numeric value, the numeric value of the calculation result, and others that are input can be displayed.

The key input unit 12 includes, for example, a numeric/arithmetic-symbol key group 12A and an application-calculation key group 12B.

The numeric/arithmetic-symbol key group 12A includes keys operated for basic calculation including four arithmetic operations, and includes, "0" to "9" (numeric) keys, a decimal key, "+", "−", "×", and "÷" (four arithmetic) keys, a "±remainder" key, a "+/−" (positive/negative inversion) key 12F, an "OFF" (off) key, a "→" key, a "C" (clear) key, an "AC" (all clear) key, an [=] (execution) key, a plurality of memory keys ([M+] key 12D, [M−] key 12E, and [MRC] key). The "÷remainder" key is a key for executing remainder calculation. The [=] (execution) key is used as an "input/confirmation" key 12C for instruction for input of a numeric value for a variable in a specified calculation formula (confirmation of input data) and transition to the subsequent calculation processing, during execution of an application calculation designated due to a key operation on the application-calculation key group 12B.

The application-calculation key group 12B includes respective keys corresponding to a plurality of application calculations for instruction for execution of calculation (application calculation) for a specific purpose. FIG. 1 illustrates an example of the application-calculation key group 12B provided with keys for executing a plurality of application calculations mainly used in hospitals, pharmacies, and others. The detail and combination of the application calculations executable in the calculator 10 are not particularly limited.

For example, the application-calculation key group 12B is provided with a "BMI" (body mass index) key 12B1, a "potency" key 12B2, a "body surface" key, and a "renal function" key. The "BMI" key is a key for executing an application that calculates a body mass index (BMI) and an ideal body weight. The "potency" key is a key for executing an application that calculates the amount of a medicine needed to exert an effect. The "body surface" key is a key for executing an application that calculates a body surface area by, for example, the Fujimoto formula or the DuBois formula. The "renal function" key is a key for executing an application that calculates, for example, creatinine clearance (CCr) (clearance of creatine in serum (the ability of the kidney to excrete body waste)) in renal function calculation, or calculates an estimated glomerular filtration rate (eGFR) in renal function calculation.

Each key included in the application-calculation key group 12B can function as a key for instruction for execution of another application calculation by a predetermined operation, for example, double pressing within a short time. For example, the "BMI" key 12B1 functions as a "powdered-medicine dispensing" key due to a double-pressing operation. Similarly, the "potency" key 12B2 functions as a "loan calculation" key, and the "renal function" key functions as a "number-of-days calculation" key.

The "powdered-medicine dispensing" key is a key for executing a post-powdered-medicine-dispensing calculation for obtaining an error range at the time of dispensing a powdered medicine. The "number-of-days calculation" key is a key for executing an application that calculates the number of elapsed days of, for example, a disease. The "loan calculation" key is a key for executing an application of loan calculation.

An application calculation executed with a key included in the application-calculation key group 12B corresponds to, for example, output (display) of a calculation result as a specific target in response to input of a data set regarding one or more items (variable names) by a predetermined data input method. In an application calculation in which a data set regarding a plurality of items (a plurality of pieces of numeric data) is input, an item as an input target is displayed on the display unit 11 as an operation guide. In response to input of numeric data for the item due to an operation on the key input unit 12, an item as the subsequent input target is displayed, and input of the subsequent numeric data is urged in a similar manner That is, in an application calculation, in order to input data for a plurality of items included in a data set, an input operation is executed in a question-and-answer format (input of a single piece of numeric data for display of a single item).

For example, in the post-powdered-medicine-dispensing calculation executed with the "powdered-medicine dispensing" key, items as input targets include "single-packet weight", "single-medicine weight", "number of powdered medicines", and "dispensing error". Thus, in execution of the post-powdered-medicine-dispensing calculation, the items "single-packet weight", "single-medicine weight", "number of powdered medicines", and "dispensing error" are displayed in this order. Due to input of respective pieces of numeric data into the items, calculation is executed on the basis of the plurality pieces of input numeric data (data set), so that an error range as the calculation result is displayed.

In such an application calculation for output (display) of a calculation result based on a data set corresponding to a plurality of items, basically, respective pieces of numeric data are input for the plurality of items for every execution of calculation.

In the calculator 10 according to the present embodiment, in input of data for a certain item, a predetermined input operation with the input of the data sets, as a default value for the certain item, the data accepted as an input, so that the default value can be used at the time of data input of the subsequent data sets. That is, a simple operation enables setting of a default value for an item as a data input target.

For example, in the post-powdered-medicine-dispensing calculation, for "single-medicine weight" and "number of powdered medicines", a different numeric value is input for each calculation because the medicine to be prescribed is different for each patient. On the other hand, the same value common to a plurality of patients may be used for the "single-packet weight" and the "dispensing error". In the calculator 10 according to the present embodiment, the respective pieces of data input for the "single-packet weight" and the "dispensing error" are each set as a default value by a predetermined input operation. Thus, there is no need to make an operation for input of the same numeric data for each calculation for the "single-packet weight" and "dispensing error" in the subsequent calculation.

For such an item with the default value set, the default value set in advance is displayed in the input state on the screen with the item as an input target displayed. This arrangement enables omission of a key operation for input of numeric data for the item.

In addition, in the calculator 10 according to the present embodiment, in input of data for a certain item, a predetermined input operation different from that for setting of the default value is made, so that non-setting of, as the default value for the certain item, the data set as the default value can be made. This arrangement facilitates a switch between setting of the default value for the certain item and non-setting of the default value for the certain item.

Figure 2:
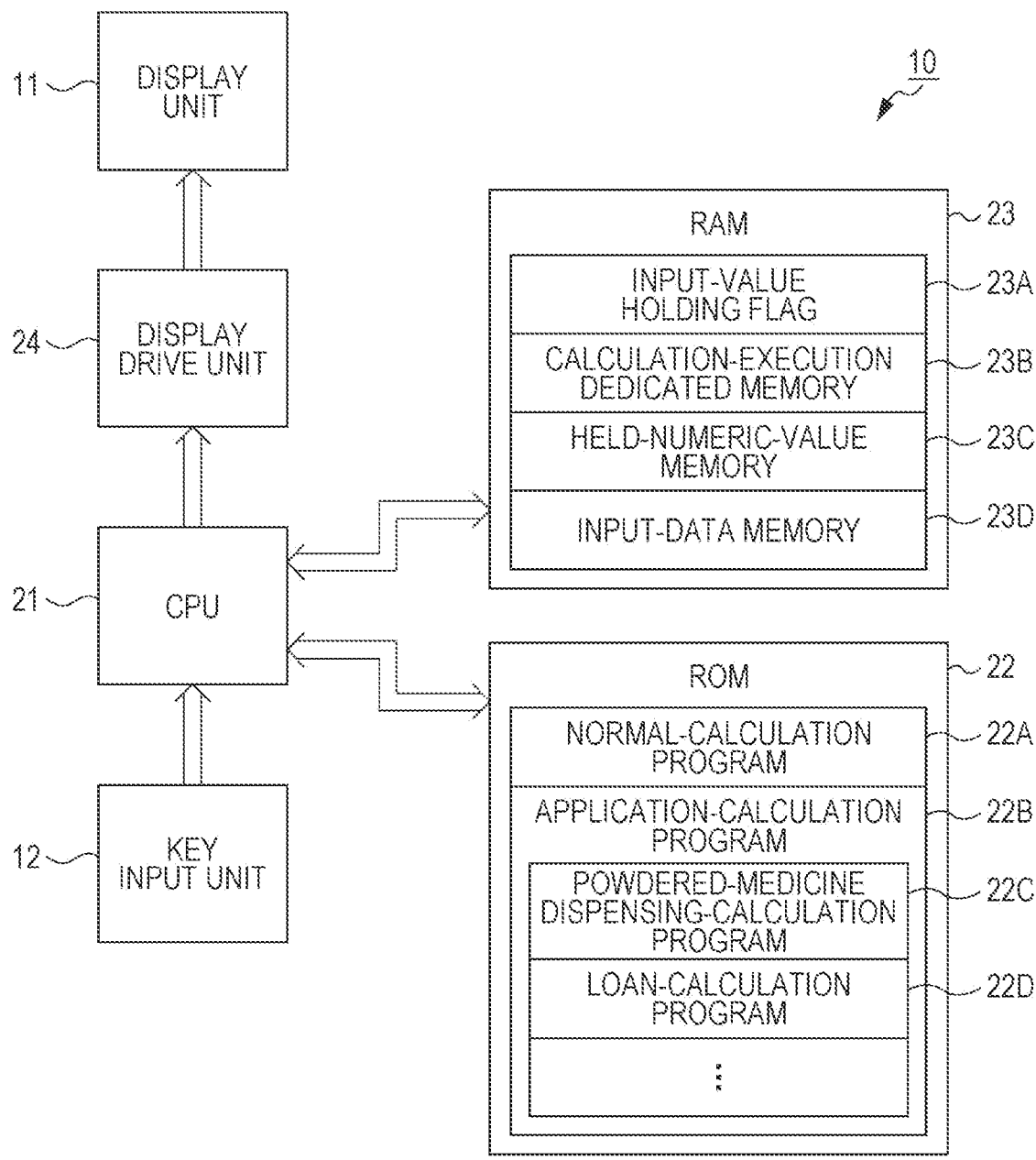
FIG. 2 is a block diagram illustrating a configuration of an electronic circuit of a calculator according to the present embodiment.

FIG. 2 is a block diagram illustrating a configuration of an electronic circuit of the calculator 10 according to the present embodiment. The electronic circuit of the calculator 10 includes a plurality of units including a central processing unit (CPU) 21 as at least one processor, and a read-only memory (ROM) 22 and a random access memory (RAM) 23 as at least one memory, achieving a computer.

The CPU 21 executes a calculation program stored in the ROM 22 to control the operation of each unit in the circuit. In response to an input operation on the key input unit 12, the CPU 21 detects a key on which the input operation is made, on the basis of a key input signal from the key input unit 12, and then executes each type of calculation processing corresponding to the key detected. The CPU 21 controls the operation of each unit in the circuit in accordance with a command described in the calculation program and software and hardware cooperate, so that the calculator 10 enables calculation processing including processing with a calculation function described in the following operation description.

The calculation programs stored in the ROM 22 include a normal-calculation program 22A and an application-calculation program 22B. The normal-calculation program 22A is a program for executing a basic calculation including four arithmetic operations. The application-calculation program 22B is a program for executing an application calculation. The application-calculation program 22B includes respective programs corresponding to a plurality of application calculations, such as a powdered-medicine dispensing-calculation program 22C to be executed in response to an operation of the "powdered-medicine dispensing" key and a loan-calculation program 22D to be executed in response to an operation of the "loan calculation" key.

Such a calculation program may be stored in the ROM 22 in advance, may be read from an external recording medium (not illustrated) such as a memory card, or may be downloaded from an external device (server or the like) through a communication unit and a communication network (including the Internet) (not illustrated).

For calculation processing by the calculation program, the RAM 23 is provided with a calculation area for storing each piece of data, in addition to an area for storing a calculation result of the calculation processing. For example, the RAM 23 is provided with an input-data memory 23D that temporarily stores data input due to a key operation on the key input unit 12, and a calculation-execution dedicated memory 23B that stores data (a numeric value) accepted as an input for the calculation processing. Further, the RAM 23 is provided with, for example, an input-value holding flag 23A and a held-numeric-value memory 23C as control areas for processing of setting data accepted as an input has for a certain item, as a default value for the certain item in an application calculation for input of a data set regarding a plurality of items.

The input-value holding flag 23A, the data stored in the calculation-execution dedicated memory 23B, and the data stored in the held-numeric-value memory 23C are managed in association with the corresponding item (variable name) as an input target. That is, the input data is stored in the calculation-execution dedicated memory 23B, and the input-value holding flag 23A is set to (ON) in response to an instruction (specific key operation) for setting of the input data as the default value for the item. The data stored in the calculation-execution dedicated memory 23B corresponding to the item with the input-value holding flag 23A set to ON is stored in the held-numeric-value memory 23C at a pre-determined timing, and is set as data of a default value corresponding to the same item. The data stored in the held-numeric-value memory 23C is treated as the data that has been input for the corresponding item, in processing of inputting a data set regarding a plurality of items of the subsequent application calculations.

In response to a key operation on the key input unit 12, the CPU 21 appropriately reads a required program, data, and others from the ROM 22, and develops and holds the program, data, and the others in the RAM 23. The CPU 21 executes a calculation operation, and outputs display data in each course of the calculation to a display drive unit 24.

The display drive unit 24 drives the display unit 11 on the basis of the display data given from the CPU 21, and displays each course of the calculation of a normal calculation and an application calculation.

First Embodiment

Next, the operation of the calculator 10 according a first embodiment will be described.

Figure 3:
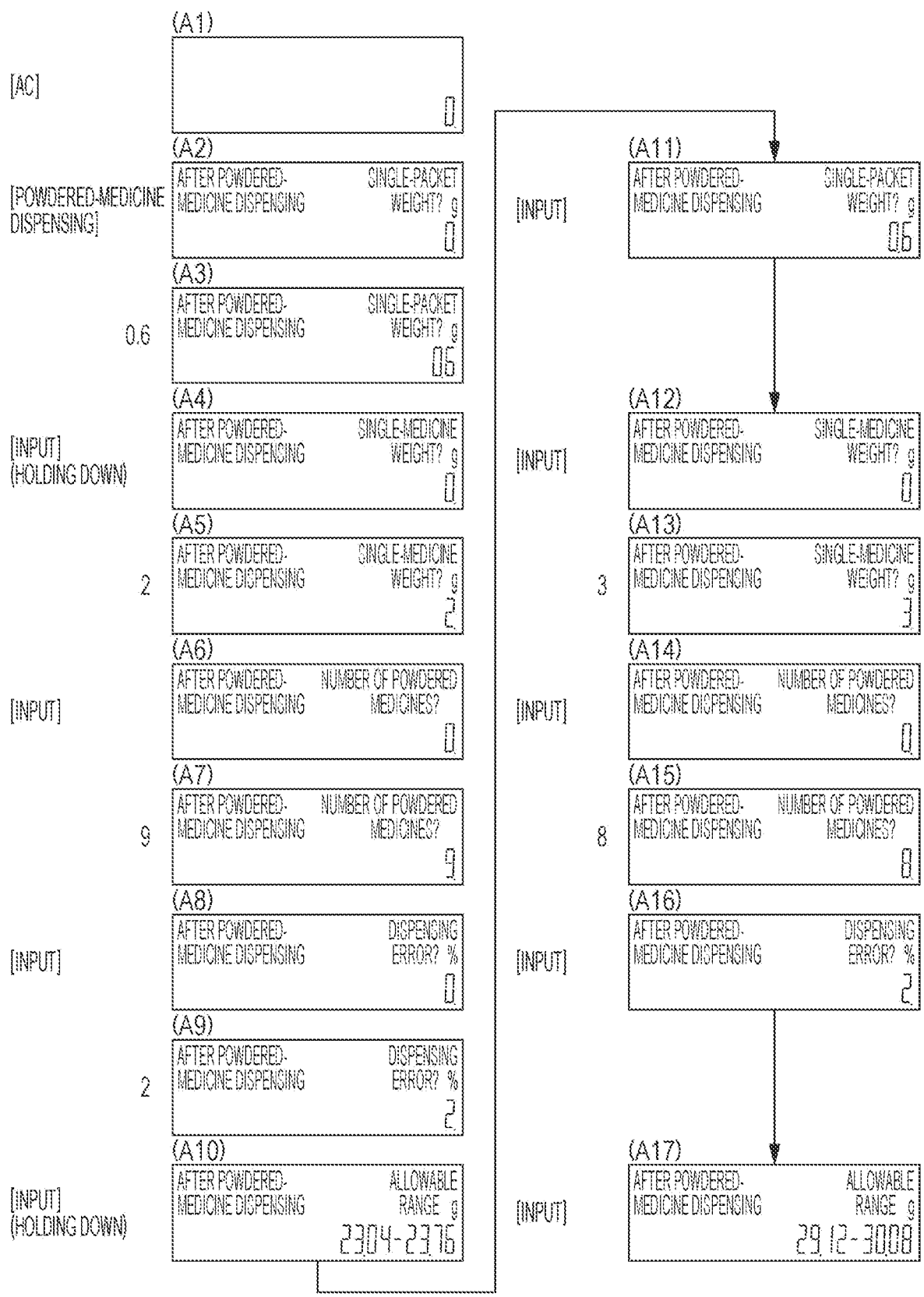
FIG. 3 illustrates a specific example of a data input operation and display for describing a calculation function of the calculator according to a first embodiment.
Figure 4:
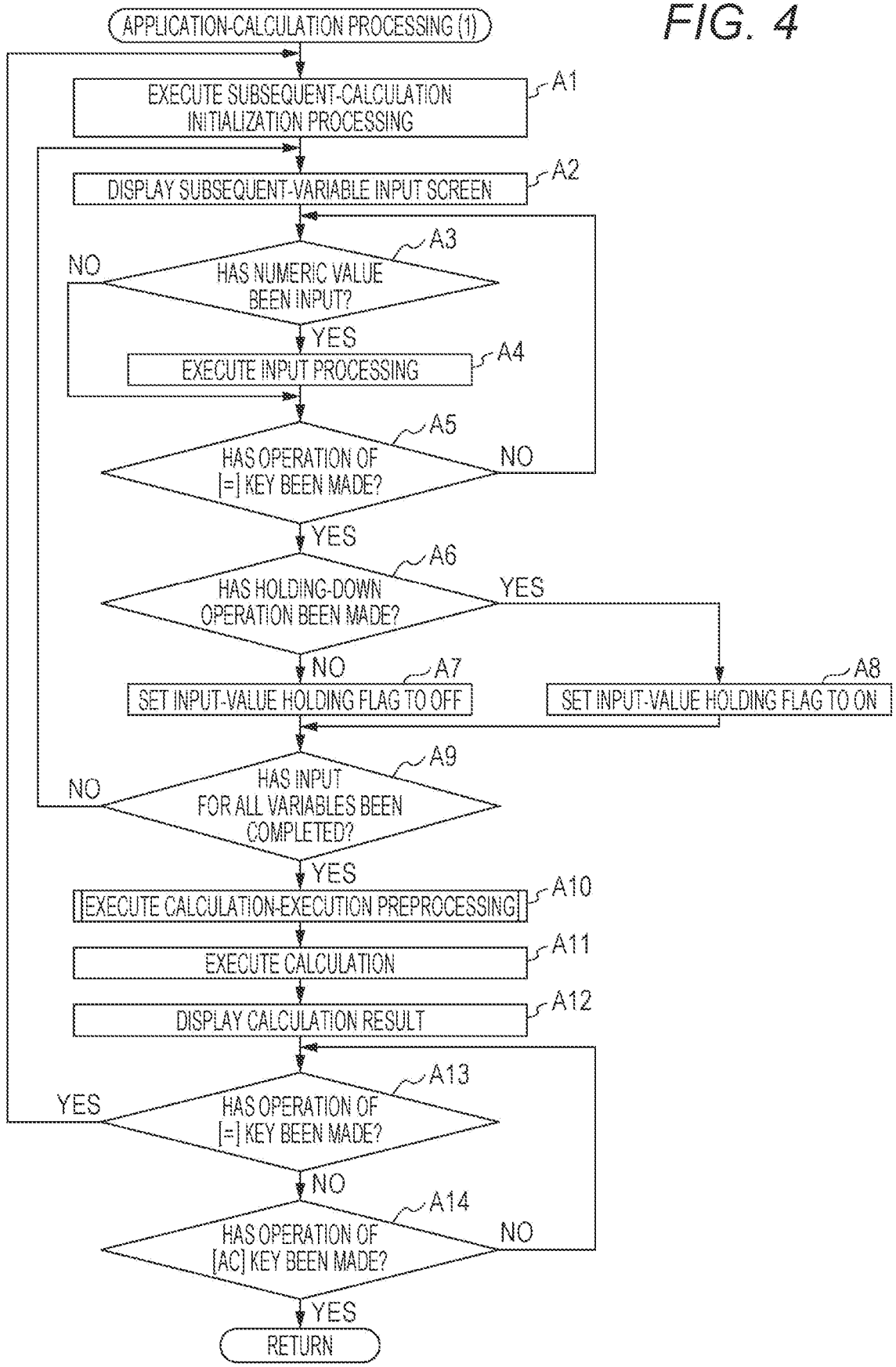
FIG. 4 is a flowchart for describing the operation of the calculation function (application-calculation processing (1)) of the calculator according to the first embodiment.
Figure 5:
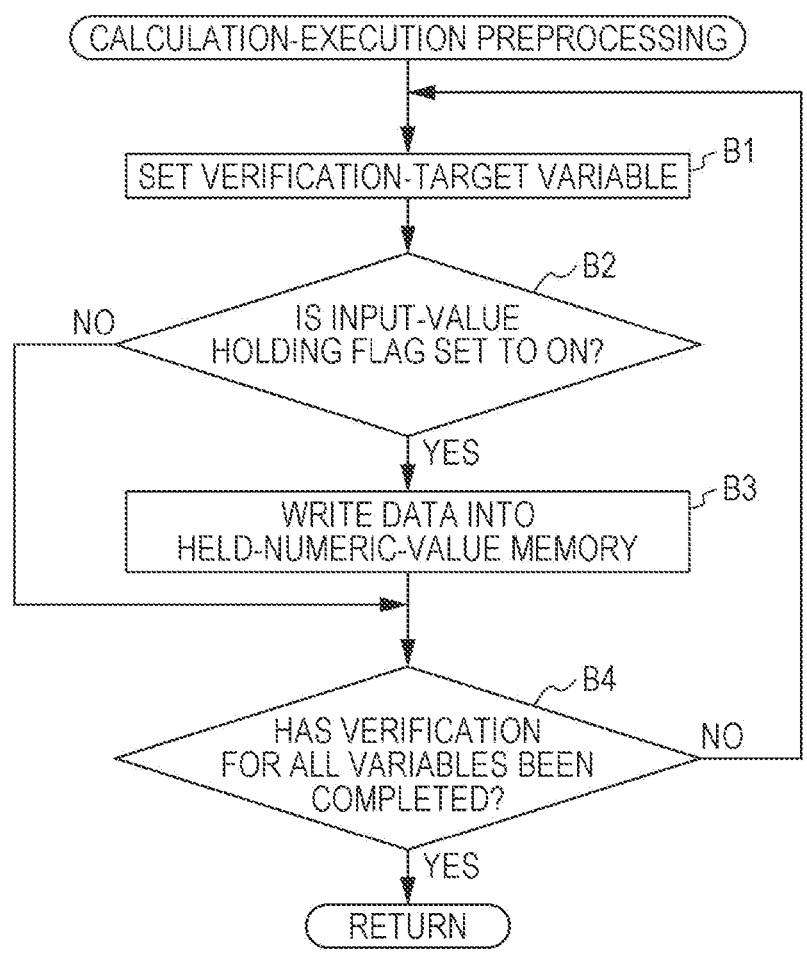
FIG. 5 is a flowchart for describing the operation of the calculation function (application-calculation processing (1)) of the calculator according to the first embodiment.

FIG. 3 illustrates a specific example of a data input operation and display for describing a calculation function of the calculator 10 according to the first embodiment. FIGS. 4 and 5 are flowcharts for describing the operation (data input method) of the calculation function (application-calculation processing (1)) of the calculator 10 according to the first embodiment. FIGS. 6A and 6B, and FIGS. 7A to 7C each illustrate a specific example of a memory image for describing a calculation function of the calculator 10 according to the first embodiment.

Here, as an example, described will be a case where an instruction for execution of an application calculation for the post-powdered-medicine-dispensing calculation is issued in response to double pressing of the "BMI" key 12B1 ("powdered-medicine dispensing" key) included in the application-calculation key group 12B.

First, in order to clear the display and the detail of the memories prior to start of the calculation, the user operates (presses down) the [AC] key. In response to the operation on the [AC] key, the CPU 21 clears all the calculation areas and control areas of the RAM 23. Further, as illustrated in (A1) of FIG. 3, the CPU 21 causes the display unit 11 to display the initial value "0" in the seven-segment display section of the lower part of the display unit 11.

In a case where the CPU 21 detects an input operation due to double pressing of the "BMI" key 12B1 ("powdered-medicine dispensing" key) immediately after the input operation of the [AC] key, the CPU 21 activates the powdered-medicine dispensing-calculation program 22C in the ROM 22 to start processing for the post-powdered-medicine-dispensing calculation. In the post-powdered-medicine-dispensing calculation in the present embodiment, data for a plurality of items (data set) is input on a question-and-answer basis (input of a single piece of numeric data for display of a single item). For example, the data set for the post-powdered-medicine-dispensing calculation includes respective pieces of data corresponding to a plurality of items "single-packet weight", "single-medicine weight", "number of powdered medicines", and "dispensing error".

After starting the post-powdered-medicine-dispensing calculation in accordance with the powdered-medicine dispensing-calculation program 22C, the CPU 21 executes initialization processing (subsequent-calculation initialization processing) for calculation of the subsequent data set (step A1). That is, the CPU 21 clears the calculation areas of the RAM 23.

Next, the CPU 21 executes the input-screen display processing to display the subsequent-variable input screen for accepting input of data for a certain item as the subsequent input target in the data set for the post-powdered-medicine-dispensing calculation (step A2).

In the input-screen display processing, the CPU 21 executes processing in a case where data is set as the default value for an item of a data set previously accepted as an input. That is, into the input-data memory 23D, the CPU 21 temporarily stores, the data stored in the held-numeric-value memory 23C corresponding to the item as an input target, as the data input for the item due to the key operation. The held-numeric-value memory 23C is in the initial state at the start of the post-powdered-medicine-dispensing calculation, and thus the data stored in the input-data memory 23D has the initial value "0".

On the subsequent-variable input screen for the post-powdered-medicine-dispensing calculation, the CPU 21 causes the display unit 11 to display, in the dot-matrix display section of the upper part thereof, the item "single-packet weight" as the subsequent data input target among the plurality of items included in the data set and the input data unit "g" corresponding to the item as the input target, in addition to the character string "after powdered-medicine dispensing" indicating the detail of the calculation as an operation guide.

Further, the CPU 21 causes the display unit 11 to display, in the seven-segment display section of the lower part thereof, a numeric character indicated by the data temporarily stored in the input-data memory 23D. At the time of data input for the first item immediately after the subsequent-calculation initialization processing, as illustrated in (A2) of FIG. 3, the CPU 21 causes the display unit 11 to display the initial value "0" in the seven-segment display section of the lower part of the display unit 11.

The CPU 21 stands by for input of a numeric value (variable) for the item "single-packet weight". Here, when detecting operations on a numeric key and the decimal key of the numeric/arithmetic-symbol key group 12A (step A3: Yes), the CPU 21 executes input processing of numeric data corresponding to the key operations. That is, the CPU 21 temporarily stores, into the input-data memory 23D, the numeric data (variable) input due to the key operations, and causes the display unit 11 to display the input numeric value. For example, in a case where the numeric data "0.6" is input, the CPU 21 causes the display unit 11 to display the numeric value "0.6" as illustrated in (A3) of FIG. 3.

If no instruction for confirmation of the input data due to an operation of the "input/confirmation" key 12C ([=] (execution) key) (step A5: No), the CPU 21 repeats input of numeric data corresponding to an operation on the numeric/arithmetic-symbol key group 12A and the input processing (steps A3 and A4).

When detecting that an operation of the "input/confirmation" key 12C has been made (step A5: Yes), the CPU 21 stores the numeric data temporarily stored in the input-data memory 23D, into the calculation-execution dedicated memory 23B in association with the item (single-packet weight) as the input target.

Further, the CPU 21 determines whether the operation made for the input of the numeric data is a first operation (first method) for an instruction for setting of, as the default value, the data input for the item as the input target.

In the first embodiment, it is assumed that an operation for input of numeric data is a combination of an operation of a numeric key (and a decimal key) for input of numeric data and an operation of the "input/confirmation" key 12C. Here, it is assumed that an operation for issuing an instruction for setting of the input data as the default value is a holding-down operation of the "input/confirmation" key 12C. In a case where the "input/confirmation" key 12C is pressed down after data is input due to an operation of a numeric key, the CPU 21 determines, in advance, whether duration in which the "input/confirmation" key 12C is continuously pressed down exceeds a reference value for determining a holding-down operation of the "input/confirmation" key 12C. It is assumed that the reference value for determining such a holding-down operation is set within a range of 300 to 500 msec, for example. Alternatively, the reference value may be a fixed value or may be changeable by a user operation.

In a case where the CPU 21 determines that the operation of the "input/confirmation" key 12C is a holding-down operation (step A6: Yes), the CPU 21 sets, to ON, the input-value holding flag 23A corresponding to the item as the input target.

FIG. 6A illustrates correspondence among an item (variable name) as an input target, the input-value holding flag 23A, data stored in calculation-execution dedicated memory 23B, and data stored in the held-numeric-value memory 23C. For example, as of now, the numeric data "0.6" accepted as an input for the item (variable name) "single-packet weight" as a data input target is stored in the calculation-execution dedicated memory 23B and it is determined that the operation of the "input/confirmation" key 12C is a holding-down operation, so that the input-value holding flag 23A corresponding to the numeric data "0.6" is set to ON.

Next, in a case where input of data for all the items (all the variables) in the data set has not been accepted, the CPU 21 executes the input-screen display processing, and causes the display unit 11 to display the subsequent-variable input screen for accepting input of data for a certain item as the subsequent input target in the data set for the post-powdered-medicine-dispensing calculation as illustrated in (A4) of FIG. 3 (step A2).

On the subsequent-variable input screen, the CPU 21 causes the display unit 11 to display, in the dot-matrix display section of the upper part thereof, the item "single-medicine weight" as the subsequent data input target among the plurality of items included in the data set and the input data unit "g" corresponding to the item as the input target, in addition to the character string "after powdered-medicine dispensing" indicating the detail of the calculation as an operation guide. Further, the CPU 21 causes the display unit 11 to display the initial value "0" in the seven-segment display section of the lower part of the display unit 11 at the time of data input for the first item immediately after the subsequent-calculation initialization processing.

The CPU 21 stands by for input of a numeric value (variable) for the item "single-medicine weight". Here, when detecting operations on a numeric key and the decimal key in the numeric/arithmetic-symbol key group 12A (step A3: Yes), the CPU 21 executes input processing of numeric data corresponding to the key operations. That is, the CPU 21 temporarily stores, into the input-data memory 23D, the numeric data (variable) input due to the key operation, and causes the display unit 11 to display the input numeric value. For example, in a case where the numeric data "2" is input, the CPU 21 causes the display unit 11 to display the numeric value "2" as illustrated in (A5) of FIG. 3.

When detecting that an operation of the "input/confirmation" key 12C has been made (step A5: Yes) after accepting the input of the numeric data "2", similarly to that described above, the CPU 21 determines whether the operation for the input of the numeric data is an operation (first operation) for instruction for setting, as the default value, the data input for the item as the input target. That is, the CPU 21 determines whether the pressing down of the "input/confirmation" key 12C operated after the data is input due to the operation of the numeric key is a holding-down operation.

In a case where the CPU 21 determines that the "input/confirmation" key 12C is pressed down after the data input due to the operation of the numeric key is not a holding-down operation (single-pressing operation) (step A6: No), that is, the CPU 21 determines that a second operation (second method) different from the first operation has been made, as illustrated in FIG. 6A, the CPU 21 sets, to OFF, the input-value holding flag 23A corresponding to the item (single-medicine weight) as the input target and the numeric data "2" accepted as an input (the default value is OFF).

As a result, as illustrated in FIG. 6A, the numeric data "2" accepted as the input for the item (variable name) "single-medicine weight" as the data input target is stored into the calculation-execution dedicated memory 23B and it is determined that the operation of the "input/confirmation" key 12C is a single-pressing operation, so that the input-value holding flag 23A corresponding to the numeric data "2" is set to OFF.

Next, similarly to that described above, the CPU 21 executes the input-screen display processing of causing the display unit 11 to display the subsequent-variable input screen for the item "number of powdered medicines" as the subsequent input target as illustrated in (A6) of FIG. 3 (step A2).

The CPU 21 stands by for input of a numeric value (variable) for the item "number of powdered medicines". Here, when detecting an operation of a numeric key in the numeric/arithmetic-symbol key group 12A (step A3: Yes), the CPU 21 executes input processing of numeric data corresponding to the key operation. That is, the CPU 21 temporarily stores, into the input-data memory 23D, the numeric data (variable) input due to the key operation, and causes the display unit 11 to display the input numeric value. For example, in a case where the numeric data "9" is input, the CPU 21 causes the display unit 11 to display the numeric value "9" as illustrated in (A7) of FIG. 3.

Here, it is assumed that the "input/confirmation" key 12C is not held down (single-pressing operation) after the data input due to the operation of the numeric key (step A6: No). As a result, as illustrated in FIG. 6A, the numeric data "9" accepted as an input is stored into the calculation-execution dedicated memory 23B for the item (variable name) "number of powdered medicines" as the data input target, and the input-value holding flag 23A corresponding to the numeric data "9" is set to OFF due to a determination that the operation of the "input/confirmation" key 12C is a single-pressing operation.

Next, similarly to that described above, the CPU 21 executes the input-screen display processing of causing the display unit 11 to display the subsequent-variable input screen for the item "dispensing error" as the subsequent input target as illustrated in (A8) of FIG. 3 (step A2).

The CPU 21 stands by for input of a numeric value (variable) for the item "dispensing error". Here, when detecting an operation of a numeric key in the numeric/arithmetic-symbol key group 12A (step A3: Yes), the CPU 21 executes input processing of numeric data corresponding to the key operation. That is, the CPU 21 temporarily stores, into the input-data memory 23D, the numeric data (variable) input due to the key operation, and causes the display unit 11 to display the input numeric value. For example, in a case where the numeric data "2" is input, the CPU 21 causes the display unit 11 to display the numeric value "2" as illustrated in (A9) of FIG. 3.

Here, it is assumed that the "input/confirmation" key 12C is held down after the data is input due to the operation of the numeric key (step A6: No). As a result, as illustrated in FIG. 6A, the numeric data "2" accepted as an input is stored in the calculation-execution dedicated memory 23B for the item (variable name) "dispensing error" as the data input target and it is determined that the operation on the "input/confirmation" key 12C is a holding-down operation, so that the input-value holding flag 23A corresponding to the numeric data "2" is set to ON.

Thus, in the first embodiment, in the combination of an operation on a numeric key for input of numeric data and an operation on the "input/confirmation" key 12C, a holding-down operation on the "input/confirmation" key 12C enables designation of the data accepted as an input, as the default value for an item as an input target.

In a case where the input (acceptance) of the data for all the items (variables) in the data set has been completed (step A9: Yes), the CPU 21 executes calculation-execution preprocessing (step A10). The calculation-execution preprocessing enables data designated as the default value for an item to be displayed as data that has been input (default value) in the input-screen display processing for data input for the subsequent data sets.

FIG. 5 is the flowchart for describing the calculation-execution preprocessing according to the first embodiment.

The CPU 21 sets an item as a verification target (as a verification-target variable) from the plurality of items included in the data set (step B1). First, the CPU 21 sets the first item "single-packet weight" in the data set for the post-powdered-medicine-dispensing calculation, and determines whether the input-value holding flag 23A corresponding to the item "single-packet weight" is set to ON. As illustrated in FIG. 6A, the input-value holding flag 23A corresponding to the item "single-packet weight" is set to ON (step B2: Yes).

In this case, the CPU 21 writes the data stored in the calculation-execution dedicated memory 23B corresponding to the item "single-packet weight", into the held-numeric-value memory 23C in association with the item "single-packet weight" (step B3). That is, the CPU 21 writes the data accepted as the input stored in the calculation-execution dedicated memory 23B into the held-numeric-value memory 23C to set the written data as the default value for the item "single-packet weight" (default-value setting processing).

In a case where verification of the respective input-value holding flags 23A for all the items in the data set has not been completed (step B4: No), the CPU 21 sets the subsequent item "single-medicine weight" as a verification-target variable, and similarly to that described above, determines whether the input-value holding flag 23A corresponding to the item "single-medicine weight" is set to ON. As illustrated in FIG. 6A, the input-value holding flag 23A corresponding to the item "single-medicine weight" is set to OFF (step B2: No). In this case, the CPU 21 does not write the data stored in the calculation-execution dedicated memory 23B corresponding to the item "single-medicine weight", into the held-numeric-value memory 23C. That is, the data accepted as the input stored in the calculation-execution dedicated memory 23B is not set as the default value for the item "single-medicine weight" (default-value non-setting processing).

Hereinafter, similarly, the CPU 21 determines whether the respective input-value holding flags 23A are set to ON for the items "number of powdered medicines" and "dispensing error". For the item "dispensing error", the input-value holding flag 23A is set to ON as illustrated in FIG. 6A. Thus, the data in the calculation-execution dedicated memory 23B corresponding to the item "dispensing error" is written into the held-numeric-value memory 23C and set as the default value.

In a case where the verification of the input-value holding flags 23A for all the items in the data set has been completed (step B4: Yes), the CPU 21 ends the calculation-execution preprocessing. As a result, for the items "single-packet weight" and "dispensing error" each having been designated by the first operation (holding down of the "input/confirmation" key 12C) for setting of the default value, the data stored in the calculation-execution dedicated memory 23B is written into the held-numeric-value memory 23C as illustrated in FIG. 6B.

After completing the calculation-execution preprocessing, the CPU 21 executes the post-powdered-medicine-dispensing calculation for obtaining an error range at the time of dispensing the powdered medicine, on the basis of the numeric data of the data set for the plurality of items stored in the calculation-execution dedicated memory 23B (step A11).

As illustrated in (A10) of FIG. 3, the CPU 21 causes the display unit 11 to display the calculation-result screen for the post-powdered-medicine-dispensing calculation (step A12). On the calculation-result screen, the CPU 21 causes the display unit 11 to display, in the dot-matrix display section of in the upper part thereof, the character string "allowable range" indicating that the displayed numeric value is the calculation result and the data unit "g", in addition to the character string "after powdered-medicine dispensing" indicating the detail of the calculation as an operation guide. Further, the CPU 21 causes the display unit 11 to display, in the seven-segment display section of the lower part thereof, the numeric characters "23.04-23.76" indicating the allowable range as the calculation result of the post-powdered-medicine-dispensing calculation.

Here, in response to an operation on the [AC] key (step A14: Yes), the CPU 21 ends the application-calculation processing for executing the post-powdered-medicine-dispensing calculation.

However, in a case where an operation on the "input/confirmation" key 12C ([=] (execution) key) has been made (step A13: Yes) with the calculation result of the post-powdered-medicine-dispensing calculation displayed, in order to transit to an application calculation (post-powdered-medicine dispensing calculation) with the subsequent data set, the CPU 21 executes initialization processing (subsequent-calculation initialization processing), and clears the calculation areas of the RAM 23 (step A1).

FIG. 7A illustrates correspondence among an item (variable name) as an input target set, the input-value holding flag 23A, data stored in the calculation-execution dedicated memory 23B, and data stored in the held-numeric-value memory 23C, at the time of transition to the post-powdered-medicine-dispensing calculation for the subsequent data set. As illustrated in FIG. 7A, the respective input-value holding flags 23A are set to ON for the items "single-packet weight" and "dispensing error" due to the data input for the data set illustrated in (A2) to (A9) in FIG. 3 described above. Thus, the pieces of data each accepted as the input are stored in the held-numeric-value memory 23C as the default value. That is, the numeric data "0.6" for the item "single-packet weight" and the numeric data "2" for the item "dispensing error" are stored as the default values in the held-numeric-value memory 23C.

Next, the CPU 21 executes the input-screen display processing to temporarily store the data stored in the held-numeric-value memory 23C corresponding to an item as an input target, into the input-data memory 23D, as the data input due to the key operation for this item (step A2).

Further, the CPU 21 causes the display unit 11 to display, in the seven-segment display section of the lower part thereof, a numeric character indicated by the data temporarily stored in the input-data memory 23D.

For the item "single-packet weight" as the subsequent input target, the accepted data "0.6" is set as the default value at the time of the data input for the previous data set. Therefore, the data in the held-numeric-value memory 23C corresponding to the item "single-packet weight" is stored into the input-data memory 23D, so that the numeric characters "0.6" is displayed on the input screen for the item "single-packet weight" in the seven-segment display section of the lower part of the display unit 11 as illustrated in (A11) of FIG. 3.

That is, on the input screen for the item "single-packet weight", the data set as the default value can be in the input state without requiring an operation on the numeric/arithmetic-symbol key group 12A.

Here, when detecting that an operation on the "input/confirmation" key 12C (step A5: Yes) has been made, the CPU 21 stores the numeric data temporarily stored in the input-data memory 23D, into the calculation-execution dedicated memory 23B in association with the item (single-packet weight) as the input target. That is, the data set in advance as the default value can be accepted by the operation on the "input/confirmation" key 12C.

Further, similarly to that described above, the CPU 21 determines whether the operation on the "input/confirmation" key 12C is a holding-down operation. In a case where the CPU 21 determines that the operation is a holding-down operation (step A6: Yes), the CPU 21 sets, to ON, the input-value holding flag 23A corresponding to the item "single-packet weight" as the input target (step A8). Otherwise, in a case where the CPU 21 determines that the operation is not a holding-down operation, (step A6: No), the CPU 21 sets, to OFF, the input-value holding flag 23A corresponding to the item "single-packet weight" as the input target (step A7). Here, it is assumed that a single-pressing operation on "input/confirmation" key 12C is made.

Next, the CPU 21 executes the input-screen display processing to cause the display unit 11 to display the subsequent-variable input screen for accepting input of data for the item "single-medicine weight" as the subsequent input target in the data set for the post-powdered-medicine-dispensing calculation as illustrated in (A12) of FIG. 3 (step A2).

As illustrated in FIG. 7A, no default value is set for the item "single-medicine weight" as illustrated in FIG. 7A, and thus the initial value "0" is displayed on the input screen. In response to input of the numeric data "3" for the item "single-medicine weight" due to an operation on the numeric/arithmetic-symbol key group 12A, the CPU 21 displays the input data "3" on the display unit 11 as illustrated in (A13) of FIG. 3. Here, in response an operation (single-pressing operation) on the "input/confirmation" key 12C, the CPU 21 stores the data "3" into the calculation-execution dedicated memory 23B in association with the item "single-medicine weight" (steps A3 to A9).

Similarly, next, the CPU 21 executes the input-screen display processing to cause the display unit 11 to display the subsequent-variable input screen for accepting input of data for the item "number of powdered medicines" as the subsequent input target in the data set for the post-powdered-medicine-dispensing calculation as illustrated in (A14) of FIG. 3 (step A2).

As illustrated in FIG. 7A, no default value is set for the item "number of powdered medicines", and thus the initial value "0" is displayed on the input screen. In response to input of the numeric data "8" due to an operation on the numeric/arithmetic-symbol key group 12A for the item "number of powdered medicines", the CPU 21 causes the display unit 11 to display the input data "8" as illustrated in (A15) in FIG. 3. Here, in response to an operation (single-pressing operation) on the "input/confirmation" key 12C, the CPU 21 stores the data "8" into the calculation-execution dedicated memory 23B in association with the item "number of powdered medicines".

Next, the CPU 21 executes the input-screen display processing to cause the display unit 11 to display the subsequent-variable input screen for accepting input of data for the item "dispensing error" as the subsequent input target in the data set for the post-powdered-medicine-dispensing calculation as illustrated in (A14) of FIG. 3 (step A2).

As illustrated in FIG. 7A, the default value is set for the item "dispensing error". Therefore, as illustrated in (A16) of FIG. 3, the default value "2" set for the item "dispensing error" is displayed on the subsequent-variable input screen for the item "dispensing error" without an operation on the numeric/arithmetic-symbol key group 12A. Here, in response to an operation (single-pressing operation) on the "input/confirmation" key 12C, the CPU 21 stores the data "2" into the calculation-execution dedicated memory 23B in association with the item "dispensing error".

In such a manner, in a case where the input (acceptance) of the data for all the items (variables) in the data set has been completed (step A9: Yes), the CPU 21 executes the calculation-execution preprocessing (step A10). In each data input for the data set illustrated in (A11) to (A16) of FIG. 3 described above, the operation on the "input/confirmation" key 12C is a single-pressing operation. Thus, the input-value holding flags 23A for all the items are set to OFF. Therefore, in the calculation-execution preprocessing, the CPU 21 does not write the data stored in the calculation-execution dedicated memory 23B, into the held-numeric-value memory 23C for any of the items. That is, the data accepted as the input is not set as the default value.

After completing the calculation-execution preprocessing, the CPU 21 executes the post-powdered-medicine-dispensing calculation on the basis of the numeric data of the data set for the plurality of items stored in the calculation-execution dedicated memory 23B (step A11), and causes the display unit 11 to display the calculation result screen for the post-powdered-medicine-dispensing calculation as illustrated in (A17) of FIG. 3 (step A12).

In such a manner, in the calculator 10 according to the first embodiment, at the time of input of data for a data set regarding a plurality of items, in the combination of an operation on a numeric key (and the decimal key) for input of numeric data and an operation on the "input/confirmation" key 12C, executed can be the default-value setting processing of setting, as the default value, the data accepted as an input for an item as an input target due to a holding-down operation on the "input/confirmation" key 12C, and executed can be the default-value non-setting processing of not setting, as the default value, the data accepted as an input for an item as an input target due to a non-holding-down (single-pressing) operation on the "input/confirmation" key 12C. On the "input/confirmation" key 12C used at the time of typical data input, the holding-down operation different from the single-pressing operation as a normal operation is made, so that the default value can be set simply.

The data set as the default value is displayed in the input state on the subsequent-variable input screen for the item as the input target. Thus, no operation on a numeric key is required, so that operation burden is reduced. In particular, in a case where input of data for a plurality of data sets is required, it is required to input data for an item having different data for each data set, so that a significant reduction in operation burden can be expected.

Note that in the example of the data input illustrated in (A11) to (A17) of FIG. 3 described above, the data for the item "single-packet weight" and the data for the item "dispensing error" each set as the default value are used without any change, respectively, as the data for the item "single-packet weight" and the data for the item "dispensing error" in the subsequent data set, however, the pieces of data can be changed freely.

FIG. 7B illustrates correspondence among an item (variable name) as an input target, the input-value holding flag 23A, data stored in the calculation-execution dedicated memory 23B, and data stored in the held-numeric-value memory 23C, in a case where data different from the data set as the default value is input.

For example, on the subsequent-variable input screen with the default value "0.6" displayed for the item "single-packet weight" illustrated in (A11) of FIG. 3, in a case where the numeric data "0.8" is input due to operations on numeric keys and a single-pressing operation of the "input/confirmation" key 12C is made, the numeric data "0.8" accepted as an input is stored into the calculation-execution dedicated memory 23B as illustrated in FIG. 7B.

Hereinafter, it is assumed that data is input due to input of numeric data and a single-pressing operation the "input/confirmation" key 12C for each of the items "single-medicine weight", "number of powdered medicines", and "dispensing error". The CPU 21 can execute an application calculation on the basis of the data of the data set input freely, regardless of the data set as the default value.

The single-pressing operations on the "input/confirmation" key 12C have been made for all the items, and thus all the input-value holding flags 23A are set to OFF as illustrated in FIG. 7B. Therefore, in calculation-execution preprocessing, the CPU 21 does not write the data stored in the calculation-execution dedicated memory 23B into the held-numeric-value memory 23C (default-value non-setting processing). As a result, the data set as the default value at the time of data input for the previous data set remains stored in the held-numeric-value memory 23C.

Therefore, at the time of input of data of the subsequent data set, for each of the items "single-packet weight" and "dispensing error" with the default values set, similarly to that described above, the subsequent-variable input screen is displayed with the data of the default value, enabling input of data with the default value.

In the example illustrated in FIG. 7B, the single-pressing operation on the "input/confirmation" key 12C is made in the input of the data for each item. However, in order to set new numeric data as the default value, it is required to hold down the "input/confirmation" key 12C.

FIG. 7C illustrates correspondence among an item (variable name) as an input target, the input-value holding flag 23A, data stored in the calculation-execution dedicated memory 23B, and data stored in the held-numeric-value memory 23C, in a case where data different from the data set as the default value is set as a default value.

For example, on the subsequent-variable input screen with the default value "0.6" is displayed for the item "single-packet weight" illustrated in (A11) of FIG. 3, in a case where the numeric data "0.8" is input due to operations on numeric keys and a holding-down operation of the "input/confirmation" key 12C is made, the input-value holding flag 23A corresponding to the item "single-packet weight" is set to ON as illustrated in FIG. 7C, and the numeric data "0.8" accepted as an input is stored in the calculation-execution dedicated memory 23B Therefore, in calculation-execution preprocessing, the input-value holding flag 23A corresponding to the item "single-packet weight" is set to ON, so that the CPU 21 writes the data stored in the calculation-execution dedicated memory 23B into the held-numeric-value memory 23C and sets the default value (default-value setting processing). In such a manner, the data accepted as an input can be simply set as a new default value.

Note that in the first embodiment, a holding-down operation (first operation) and a single-pressing operation (second operation) on the "input/confirmation" key 12C to be typically operated for confirmation of input data correspond, respectively, to control of setting of the default value and control of non-setting of the default value; however, control of setting and control of non-setting of the data accepted as an input, as the default value, may each correspond to a different key operation from the above. For example, instead of the holding down operation, the "input/confirmation" key 12C and another key may be pressed simultaneously.

Second Embodiment

Next, the operation of a calculator 10 according to a second embodiment will be described.

Figure 8:
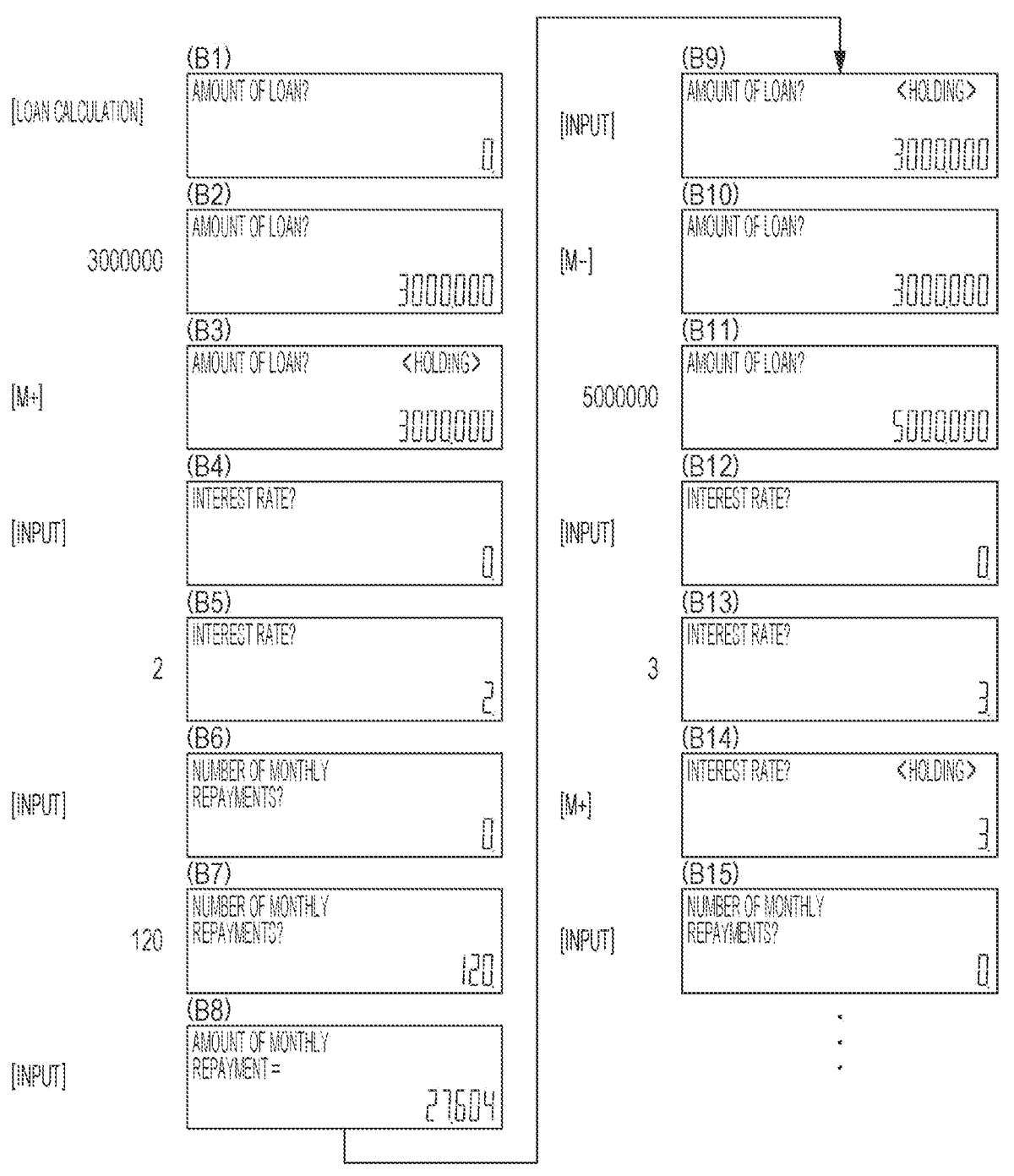
Figure 9:
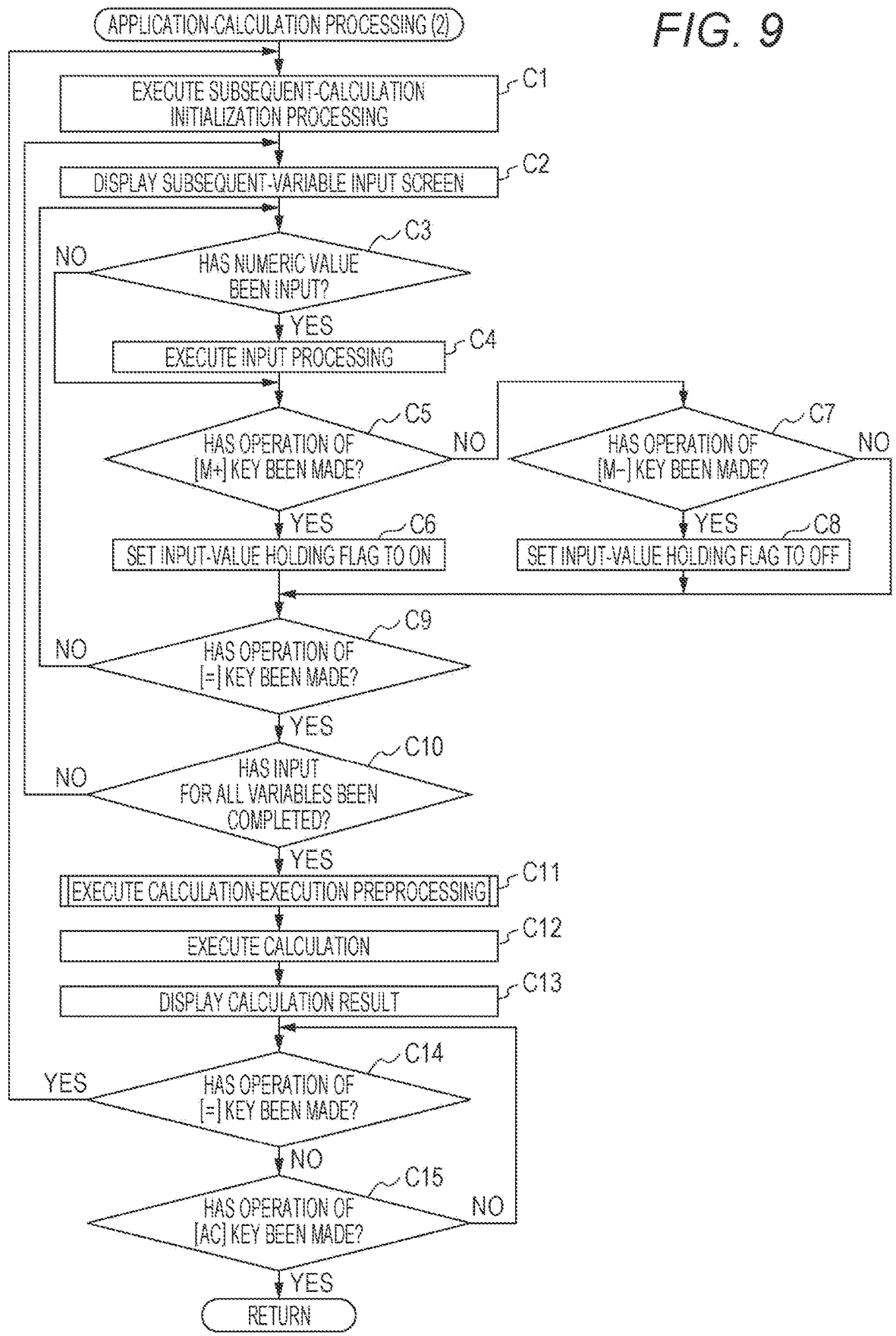
FIG. 9 is a flowchart for describing the operation of the calculation function (application-calculation processing (2)) of the calculator according to the second embodiment.

FIG. 8 illustrates a specific example of a data input operation and display for describing a calculation function of the calculator 10 according to the second embodiment. FIG. 9 is a flowchart for describing the operation (data input method) of the calculation function (application-calculation processing (2)) of the calculator 10 according to the second embodiment.

In the first embodiment, in the combination of an operation of a numeric key for input of numeric data and an operation of the "input/confirmation" key 12C, a holding-down operation and a single-pressing operation of the "input/confirmation" key 12C correspond, respectively, to control of setting of the data accepted as an input, as the default value, and control of non-setting of the data accepted as an input, as the default value. In the second embodiment, in the combination of an operation of a numeric key for input of numeric data and an operation of a specific key determined in advance, making of a specific key operation (first operation) and non-making of a specific operation (second operation) correspond, respectively, to control of setting of the data accepted as an input, as the default value (default-value setting processing) and control of non-setting of the data accepted as an input, as the default value (default-value non-setting processing).

In the second embodiment, it is assumed that, for example, an [M+] key 12D and an [M−] key 12E of memory keys are each used as a specific key determined in advance. It is assumed that the [M+] key 12D is used for an operation for setting of the data accepted as an input, as the default value (first operation), and the [M−] key 12E is used for an operation for not setting of the data accepted as an input, as the default value (second operation).

Note that the [M+] key 12D and the [M−] key 12E are keys that are not used in an application calculation, and thus are used as specific keys for setting of the default value. In a case where a key that is different from the [M+] key 12D and the [M−] key 12E and that is not used for data input in an application calculation is present in a key input unit 12, this key can be used as a specific key.

Here, as an example, described will be a case where an instruction for execution of an application calculation for loan calculation is issued in response to double pressing of a "potency" key 12B2 included in an application-calculation key group 12B ("loan calculation" key).

Note that the application-calculation processing (2) in the second embodiment is basically the same as the application-calculation processing (1) in the first embodiment, and thus the description of the common parts will be omitted.

In a case where a CPU 21 detects an input operation due to double pressing of the "potency" key 12B2 ("loan calculation" key) immediately after an input operation of an [AC] key, the CPU 21 activates a loan-calculation program 22D in a ROM 22 to start processing for the loan calculation. In the loan calculation according to the present embodiment, it is assumed that a data set includes respective pieces of data corresponding to a plurality of items "amount of loan", "interest rate", and "number of monthly repayments", and the amount of monthly repayment is calculated as the calculation result.

After executing initialization processing (subsequent-calculation initialization processing) (step C1), the CPU 21 executes input-screen display processing, and causes a display unit 11 to display the subsequent-variable input screen for accepting input of data for the item "amount of loan" as the subsequent input target in the data set for the loan calculation (step C2).

As illustrated in (B1) of FIG. 8, the CPU 21 causes the display unit 11 displays, on the subsequent-variable input screen thereof, the character string of the item "amount of loan" as the subsequent input target and the initial value"0".

Here, in a case were the numeric data "3000000" is input due to operations of numeric keys in a numeric/arithmetic-symbol key group 12A, the CPU 21 executes input processing and causes the display unit 11 to display the numeric value"3000000" as illustrated in (B2) of FIG. 8 (steps C3 and C4).

In a case where no instruction for input data confirmation is issued due to an operation of a "input/confirmation" key 12C ([=] (execution) key)(step C9: No), the CPU 21 repeats input of numeric data corresponding to an operation on the numeric/arithmetic-symbol key group 12A and the input processing.

In a case where an operation of the [M+] key 12D has been made before the operation of the "input/confirmation" key 12C (step C5: Yes), the CPU 21 sets, to ON, the input-value holding flag 23A corresponding to the item "amount of loan" as the input target (step C6). That is, the numeric data displayed on the input screen is set as the default value.

In response to the operation of the [M+] key 12D, the CPU 21 causes the display unit 11 to display in a dot-matrix display section thereof, setting information indicating that the input data is to be set (held) as the default value as illustrated in (B3) of FIG. 8. In (B3) of FIG. 8, for example, the character string "<holding>" is displayed as the setting information to notify the user that the default value is to be set.

Note that, as a notification method, not only the character string "<holding>" can be displayed on the display unit 11 as a setting guide as illustrated in (B3) of FIG. 8, but also a form different from such character display, for example, change of the background color of the display unit 11 or display by blinking of an input numeric value (default value) as well as a sound output or a light emitting diode (LED) display (lightning, blinking) determined in advance can be used.

When detecting that an operation of the "input/confirmation" key 12C has been made (step C9: Yes), the CPU 21 stores the input numeric data in association with the item (amount of loan) as the input target.

Next, in a case where input of data for all the items (all the variables) in the data set has not been accepted, the CPU 21 executes the input-screen display processing, and causes the display unit 11 to display the subsequent-variable input screen for accepting input of data for the item "interest rate" as the subsequent input target as illustrated in (B4) of FIG. 8 (step C2).

Here, in response to input of the numeric data "2" due to an operation of a numeric key (steps C3 and C4), the CPU 21 causes the display unit 11 to display the input numeric value "2" as illustrated in (B5) of FIG. 8. Further, in response to an operation of the "input/confirmation" key 12C is (step C9: Yes), the CPU 21 stores the numeric value "2" in association with the item "interest rate".

Similarly, the CPU 21 executes the input-screen display processing, and causes the display unit 11 to display the subsequent-variable input screen for accepting input of data for the item "number of monthly repayments" as the subsequent input target as illustrated in (B6) of FIG. 8 (step C2). In response to input of the numeric data "120" for the item "number of monthly repayments", the CPU 21 causes the display unit 11 to display the input numeric value "120" as illustrated in (B7) of FIG. 8.

Further, in response to an operation of the "input/confirmation" key 12C (step C9: Yes), the CPU 21 stores the numeric value "120" in association with the item "number of monthly repayments".

Here, because the input of the data for all the items in the data set has been completed (step C10: Yes), the CPU 21 executes calculation-execution preprocessing, and sets the data "3000000" accepted as the input for the item "amount of loan" with the input-value holding flag 23A set to ON in response to the operation of the [M+] key 12D, as the default value of this item (Step C11).

The CPU 21 executes the loan calculation on the basis of the data input for all of the items in the data set (step C12), and causes the display unit 11 to display the amount of monthly repayment "27604" as the calculation result as illustrated in (B8) of FIG. 8.

Here, in response to an operation of the [AC] key (step C15: Yes), the CPU 21 ends the application-calculation processing for executing the loan calculation.

However, in a case where an operation of the "input/confirmation" key 12C has been made with the calculation result of the loan calculation displayed (step C13: Yes), in order to transit to the application calculation (loan calculation) with the subsequent data set, the CPU 21 executes the initialization processing (subsequent-calculation initialization processing) (step C1), and then executes the input-screen display processing to cause the display unit 11 to display the subsequent-variable input screen for accepting data input for the item "amount of loan" as the subsequent input target in the data set for the loan calculation (step C2).

Here, because the default value is set for the item "amount of loan", the CPU 21 causes the display unit 11 to display the default value"3000000" on the subsequent-variable input screen variable of the display unit 11 as illustrated in (B9) of FIG. 8. Further, the CPU 21 causes the display unit 11 to display information indicating that the data set (held) as the default value is displayed, on the subsequent-variable input screen with the default value displayed. In (B3) of FIG. 8, for example, the character string "<holding>" is displayed to notify the user that the default value is to be set. As a notification method, a form different from such character display can be also adopted as described above. Alternatively, a notification may be issued in a form different from an instruction for setting of the default value.

In the second embodiment, for an item with the default value set due to an operation of the [M+] key 12D, no change is made for the default value for this item (locked). That is, in a case where the subsequent-variable input screen (character string "<holding>" as setting information) is displayed with the default value, when detecting an operation of a numeric key (Step C3: Yes), the CPU 21 invalidates input of numeric data corresponding to the key operation and does not input data corresponding to the key operation in the input processing. In this case, in order to issue a notification that data input due to the key operation is invalidated, the CPU 21 may cause the display unit 11 to display predetermined information.

In such a manner, invalidation of data input for an item with the default value set can reliably avoid execution of calculation due to input of erroneous data for the item with the default value set in advance.

In a case where an operation of the "input/confirmation" key 12C has been made with the subsequent-variable input screen displayed with the default value, the CPU 21 executes processing of the default value as input data for the item as an input target, similarly to the first embodiment.

However, in a case where input of a numeric value different from the default value is preferable, an operation of the [M−] key 12E enables the default value set for the item as the input target to be initialized at the time of data input.

As illustrated in (B9) of FIG. 8, in a case where an operation the [M−] key 12E has been made with the default value "3000000" displayed on the subsequent-variable input screen variable for the item "amount of loan" (step C7: Yes), the CPU 21 sets, to OFF, the input-value holding flag 23A corresponding to the item "amount of loan" (step C8).

In this case, as illustrated in (B10) of FIG. 8, the CPU 21 deletes the character string "<holding>" displayed on the display unit 11, and validates data input due to an operation on the numeric/arithmetic-symbol key group 12A (a numeric key).

Here, in response to input of the numeric data "5000000" for the item "amount of loan" due to operations on numeric keys (step C3: Yes), the CPU 21 causes the display unit 11 to display the input numeric value "5000000" subjected to the input processing as illustrated in (B11) of FIG. 8.

Here, when detecting that an operation of the "input/confirmation" key 12C has been made (step C9: Yes), the CPU 21 stores the input numeric data "5000000" in association with the item (amount of loan) as the input target.

Next, the CPU 21 executes the input-screen display processing to cause the display unit 11 to display the subsequent-variable input screen for accepting data input for the item "interest rate" as the subsequent input target as illustrated in (B12) of FIG. 8 (step C2).

Here, in response to input of the numeric data "3" due to an operation of a numeric key (steps C3 and C4), the CPU 21 displays the input numeric value "3" as illustrated in (B14) in FIG. 8.

Here, in a case where an operation of the [M+] key 12D has been made (step C5: Yes), the CPU 21 sets, to ON, the input-value holding flag 23A for the item "interest rate", and causing the display unit 11 to display the input numeric value "3" and the character string "<holding>" as illustrated in (B14) of FIG. 8.

Further, in response to an operation of the "input/confirmation" key 12C (step C9: Yes), the CPU 21 stores the numeric value "3" in association with the item "interest rate".

Hereinafter, similarly to that described above, executed is processing of inputting data for an item as the subsequent input target. In a case where the input of the data for all the items (all the variables) in the data set has been completed (step C10: Yes), the CPU 21 executes the calculation-execution preprocessing (step C11).

In the example illustrated in (B9) to (B15) of FIG. 8, the input-value holding flag 23A corresponding to the item "amount of loan" is set to OFF, and the input-value holding flag 23A corresponding to the item "interest rate" is set to ON.

In the calculation-execution preprocessing of the second embodiment, for an item with the input-value holding flag 23A set to OFF, the data stored in a calculation-execution dedicated memory 23B is not written into a held-numeric-value memory 23C, and the default value stored in the held-numeric-value memory 23C is initialized (the numeric value "0" is written). Therefore, at the time of data input for the subsequent data set, no default value is set for the item "amount of loan" (the initial value "0" is set), and the numeric value "0" is displayed in the initial state of the subsequent-variable input screen, so that any piece of data can be input.

In such a manner, in the calculator 10 according to the second embodiment, at the time of input of data for a data set regarding a plurality of items, in the combination of an operation of a numeric key (and the decimal key) for input of numeric data and an operation of the "input/confirmation" key 12C, executed can be the default-value setting processing of setting, as the default value, the data accepted as an input for an item as an input target due to an operation of the [M+] key 12D determined in advance, and executed can be the default-value non-setting processing of not setting, as the default value, the data accepted as an input for an item as an input target due to an operation of the [M−] key 12E. An intuitive operation of the [M+] key 12D and an intuitive operation of the [M−] key 12E used as specific keys facilitate designation of setting of input data as the default value and non-setting of input data as the default value, respectively.

Note that in the second embodiment described above, data input is invalidated for an item with the default value set; however, data input may be validated and a numeric value may be changed even if no operation of the [M−] key 12E is made. In this case, it is assumed that the default value set for the item is not initialized unless an operation of the [M−] key 12E is made with the default value displayed. In addition, with data input validated for an item with the default value set, in a case where an operation of a numeric key and an operation (first operation) of setting of the default value due an operation of the [M+] key 12D have been made, if the set default value is not released due to an operation of the [M−] key 12E, non-setting (non-change) of the default value using the accepted data is made.

In the above description, the [M+] key 12D and the [M−] key 12E are used as the specific keys for setting of the default value for an item. Setting of the default value or initialization of the default value may be designated with a single specific key.

For example, it is assumed that a "+/−" key 12F is used as a specific key. In this case, for an item as an input target with no default value set, in a case where an operation of the "+/−" key 12F has been made before an operation of the "input/confirmation" key 12C after data input, the input data is set as the default value. Alternatively, in a case where an operation of the "+/−" key 12F has been made with the default value displayed on the subsequent-variable input screen, the default value set for the item as the input target is initialized.

In such a manner, a toggle operation of a single specific key ("+/−" key 12F) enables control of setting of the default value for an item and initialization of the default value for an item, and enables a switch between display of setting information on the display and non-display of setting information on the display unit 11. This arrangement simplifies a key operation, and enables effective utilization of keys in a case where the number of keys that a key input unit 12 is provided with is limited.

Note that in the first and second embodiments described above, a single default value is set for a single item; however, a plurality of default values may be set for a single item. For example, in the second embodiment, with data input for a certain item set as the default value, in a case where an instruction is issued that the default value is set for the data input for the same item in the same data set or a different data set, a new default value is set as the default value in association with the same item.

On the subsequent-variable input screen for an item with a plurality of default values set, any one of the plurality of default values is selected and displayed on the initial screen. For example, the latest default value added or the default value having the largest number of times of input confirmation (operation of "input/confirmation" key 12C) is selected from the plurality of default values. In a case where a default value different from the default value displayed on the subsequent-variable input screen is used, the display is switched to the different default value in response to an operation of, for example, a "→" key of the key input unit 12, so that any one of the plurality of default values can be selected.

Furthermore, in the first and second embodiments described above, given has been an example of executing calculation based on the data (numeric value) input for one or more items in the calculator 10. However, the data input method in the present embodiment is applicable to data input processing in an information processing apparatus that inputs different data.

For example, in addition to input of numeric data for calculation, the input method is applicable to data input processing in an information processing apparatus that inputs data in various formats such as text data, image data, and graphic data for a plurality of items. The types of data input to the plurality of items may be, for example, numeric data, text data, image data, and graphic data, and a mixture of such pieces of data may be input.

As a program executable by a computer, the data input method to be executed by the electronic device described in the embodiments can be distributed by being stored in a recording medium such as a memory card (ROM card, RAM card, and or the like), a magnetic disk (flexible disk, hard disk, or the like), an optical disk (compact disc (CD)-ROM, digital versatile disc (DVD), or the like), or a semiconductor memory. The computer reads the program recorded in such an external recording medium and the operation is controlled by the program, enabling processing similar to the functions described in the embodiments.

The data of each program for achievement of the corresponding technique can be transmitted on a network (such as the Internet) in the form of a program code, and the program data can be fetched from a computer (such as a server device) connected to the network to achieve functions similar to those of the above embodiments.

Note that the invention of the present application is not limited to the embodiments, and thus various modifications can be made in an embodiment stage without departing from the gist of the invention. Further, the embodiments include inventions at various stages, and thus various inventions can be extracted by an appropriately combination of a plurality of disclosed constituent features. For example, even if some constituent features are deleted from or some constituent features are combined in all of the constituent features indicated in the embodiments, when the issues described in Related Art can be solved and the effects described in Summary can be obtained, a configuration in which these constituent features are deleted or combined can be extracted as the invention.

What is claimed is:

1. An electronic device comprising at least one processor configured to execute a program stored in at least one memory,
wherein the at least one processor
executes input-screen display processing of causing a display to display an input screen, in order to accept input of data for a certain item,
executes, in a case where the input of the data for the certain item is accepted by a first method during display of the input screen, default-value setting processing of setting the data as a default value for the certain item, and executes data processing with the data of which the input is accepted by the first method, and
executes, in a case where the input of the data for the certain item is accepted by a second method different from the first method during display of the input screen, default-value non-setting processing of not setting, as the default value for the certain item, the data of which the input is accepted, and executes the data processing with the data of which the input is accepted by the second method.

2. The electronic device according to claim 1,
wherein in a case where the input-screen display processing is executed after the default-value setting processing is executed, the at least one processor causes the display to display the default value as the data for the certain item on the input screen.

3. The electronic device according to claim 1,
wherein in a case where the input-screen display processing is executed after the default-value setting processing is executed, the at least one processor causes the display to display setting information indicating that the default value is set as the data for the certain item.

4. The electronic device according to claim 1,
wherein the at least one processor
executes, after accepting input of data for all items in a data set including the certain item, with a fact stored that the input of the data is accepted by the first method, the default-value setting processing, and
executes, after accepting the input of the data for all the items in the data set, with a fact stored that the input of the data is accepted by the second method, the default-value non-setting processing.

5. The electronic device according to claim 4,
wherein the at least one processor
stores the data in a first memory in a case where the input of the data is accepted for the certain item by the first method,
executes, after accepting the input of the data for all the items in the data set, as the default-value setting processing, processing of storing, as the default value, the data stored in the first memory into a second memory, and
executes, after accepting the input of the data for all the items in the data set, as the default-value non-setting processing, processing of not storing the data stored in the first memory into the second memory.

6. The electronic device according to claim 1,
wherein the at least one processor executes, in a case where the default value is set for the certain item, as the default-value non-setting processing, processing of initializing the default value in accordance with the acceptance of the input of the data by the second method.

7. The electronic device according to claim 1,
wherein in a case where the input-screen display processing is executed after the default-value non-setting processing is executed, the at least one processor causes the default value not to be displayed as the data for the certain item.

8. The electronic device according to claim 1,
wherein the acceptance of the input of the data by the first method includes an operation of a numeric key and an operation of a specific key, and
the acceptance of the input of the data by the second method includes an operation of a numeric key and another operation of the specific key.

9. The electronic device according to claim 1,
wherein the acceptance of the input of the data by the first method includes an operation of a numeric key and an operation of a first specific key, and
the acceptance of the input of the data by the second method includes an operation of a numeric key and an operation of a second specific key different from the first specific key.

10. The electronic device according to claim 1,
wherein the at least one processor causes the display to display a notification for setting information indicating that the data is to be set as the default value of the certain item.

11. The electronic device according to claim 10,
wherein the at least one processor makes a switch, due to a predetermined operation, between a state where the notification for the setting information is displayed on the display and a state where no notification for the setting information is displayed on the display.

12. The electronic device according to claim 10,
wherein the at least one processor keeps the input of the data for the certain item invalidated while the display is displaying the notification for the setting information.

13. The electronic device according to claim 10,
wherein the at least one processor keeps the input of the data for the certain item validated while the display is displaying no notification for the setting information.

14. The electronic device according to claim 10,
wherein the at least one processor executes the default-value setting processing in a case where a confirmation operation of the input of the data for the certain item is accepted while the display is displaying the notification for the setting information.

15. The electronic device according to claim 10,
wherein the at least one processor executes the default-value non-setting processing in a case where a confirmation operation of the input of the data for the certain item is accepted while the display is displaying no notification for the setting information.

16. The electronic device according to claim 1,
wherein the at least one processor
executes, after completion of input of data for all items in a data set including the certain item, default-value display processing of causing the display to display the data of which the input is accepted by the first method, and
executes, during display of the data by the display, default-value no-setting processing of making a change such that the data of which the input is accepted by the first method is not set as the default value of the certain item.

17. The electronic device according to claim 1,
wherein the at least one processor
executes the data processing after accepting input of data for all items in a data set including the certain item, and
executes the data processing after accepting the input of the data for all the items of the data set.

18. A data input method to be executed by at least one processor in an electronic device, the data input method comprising the steps of:
  executing input-screen display processing of causing a display to display an input screen, in order to accept input of data for a certain item;
  executing, in a case where the input of the data for the certain item is accepted by a first method during display of the input screen, default-value setting processing of setting the data as a default value for the certain item, and executing data processing with the data of which the input is accepted by the first method; and
  executing, in a case where the input of the data for the certain item is accepted by a second method different from the first method during display of the input screen, default-value non-setting processing of not setting, as the default value for the certain item, the data of which the input is accepted, and executing the data processing with the data of which the input is accepted by the second method.

19. A non-transitory computer-readable recording medium storing a program for causing a processor to realize:
  a function of executing input-screen display processing of causing a display to display an input screen, in order to accept input of data for a certain item;
  a function of executing, in a case where the input of the data for the certain item is accepted by a first method during display of the input screen, default-value setting processing of setting the data as a default value for the certain item and executing data processing with the data of which the input is accepted by the first method; and
  a function of executing, in a case where the input of the data for the certain item is accepted by a second method different from the first method during display of the input screen, default-value non-setting processing of not setting, as the default value for the certain item, the data of which the input is accepted and executing the data processing with the data of which the input is accepted by the second method.

* * * * *